US010792293B2

(12) United States Patent
Kelidari et al.

(10) Patent No.: US 10,792,293 B2
(45) Date of Patent: Oct. 6, 2020

(54) TOPICAL NANODRUG FORMULATION (71) Applicants: Hamidreza Kelidari, Tehran (IR); Majid Saeedi, Sari (IR)

(72) Inventors: Hamidreza Kelidari, Tehran (IR); Majid Saeedi, Sari (IR)

(*) Notice: Subject to any disclaimer, the term of this patent is extended or adjusted under 35 U.S.C. 154(b) by 0 days.

(21) Appl. No.: 15/163,724

(22) Filed: May 25, 2016

(65) Prior Publication Data
US 2017/0020896 A1 Jan. 26, 2017

Related U.S. Application Data

(60) Provisional application No. 62/199,473, filed on Jul. 31, 2015.

(51) Int. Cl.
*A61K 31/585* (2006.01)
*A61K 9/00* (2006.01)
*A61K 9/107* (2006.01)
*A61K 9/51* (2006.01)

(52) U.S. Cl.
CPC .......... *A61K 31/585* (2013.01); *A61K 9/0014* (2013.01); *A61K 9/107* (2013.01); *A61K 9/5123* (2013.01)

(58) Field of Classification Search
CPC .... A61K 31/585; A61K 9/0014; A61K 9/107; A61K 9/5123; H05K 7/20918
See application file for complete search history.

(56) References Cited

U.S. PATENT DOCUMENTS

| | | | |
|---|---|---|---|
| 4,543,351 A * | 9/1985 | Messina | A61K 8/63 514/175 |
| 5,667,800 A | 9/1997 | De Vringer | |
| 6,028,098 A * | 2/2000 | Goodman | A61K 8/4946 514/427 |
| 8,003,690 B2 * | 8/2011 | Vergnault | A61K 9/0014 514/462 |
| 8,663,692 B1 * | 3/2014 | Muller | A61K 9/0014 424/401 |

FOREIGN PATENT DOCUMENTS

WO    WO2012176212 A1    12/2012

OTHER PUBLICATIONS

Zouaoui Bourezg, Redispersible lipid nanoparticles of Spironolactone obtained by three drying methods, Colloids and Surfaces A: Physicochem. Eng. Aspects, Mar. 21, 2012, vol. 413, pp. 191-199.
P. Langguth, Nanosuspension Formulations for Low-Soluble Drugs: Pharmacokinetic Evaluation Using Spironolactone as Model Compound, Drug Development and Industrial Pharmacy, 2005, vol. 31, pp. 319-329.

(Continued)

*Primary Examiner* — Snigdha Maewall
(74) *Attorney, Agent, or Firm* — Bajwa IP Law Firm; Haris Zaheer Bajwa (57) ABSTRACT

A formulation includes a nanostructured lipid carrier (NLC) matrix and spironolactone as an active ingredient loaded within the NLC matrix, forming a spironolactone-loaded NLC (SP-NLC) gel or lotion.

17 Claims, 7 Drawing Sheets

(56) References Cited

OTHER PUBLICATIONS

Rehab Nabil Shamma, Follicular delivery of spironolactone via nanostructured lipid carriers for management of alopecia, Nov. 26, 2014, International Journal of Nanomedicine, vol. 9, pp. 5449-5460.
Golnar Dorraj, Preparation of SLN-containing Thermoresponsive In-situ Forming Gel as a Controlled Nanoparticle Delivery System and Investigating its Rheological, Thermal and Erosion Behavior, Iranian Journal of Pharmaceutical Research, May 2014, vol. 14, Issue 2, pp. 347-358.
Zhinan Mei, Triptolide Loaded Solid Lipid Nanoparticle Hydrogel for Topical Application, Drug Development and Industrial Pharmacy, 2005, vol. 31, pp. 161-168.
Fu-Qiang Hu, Preparation and characterization of stearic acid nanostructured lipid carriers by solvent diffusion method in an aqueous system, Colloids and Surfaces B: Biointerfaces, Sep. 27, 2005, vol. 45, pp. 167-173.
Wei Liu, Investigation of the carbopol gel of solid lipid nanoparticles for the transdermal iontophoretic delivery of triamcinolone acetonide acetate, International Journal of Pharmaceutics, Aug. 22, 2008, vol. 364, 135-141.
E.B. Souto, Evaluation of the physical stability of SLN and NLC before and after incorporation into hydrogel formulations, European Journal of Pharmaceutics and Biopharmaceutics, May 7, 2004, vol. 58, pp. 83-90.

\* cited by examiner

TOPICAL NANODRUG FORMULATION

CROSS REFERENCE TO RELATED APPLICATION

The present application claims priority from U.S. Provisional Patent Application Ser. No. 62/199,473, filed Jul. 31, 2015, entitled "SPIRONOLACTONE NANOGEL FORMULATION", which is incorporated by reference herein in its entirety.

TECHNICAL FIELD

The present application generally relates to a topical drug formulation including spironolactone as an active ingredient loaded onto a nano-structured lipid carrier (SP-NLC), and a method for the preparation and therapeutic use thereof.

BACKGROUND

Acne vulgaris is a disorder of the pilosebaceous unit, characterized by comedones, inflammatory lesions and scars on the face, chest, and back. It is estimated that 80-95% of adolescents suffer from acne at some point in their lives and in some cases the acne will continue into their adulthood. Although, acne and other skin disorders that respond to anti-androgens include rosacea, androgenic alopecia, hirsutism, and the like, are not life threatening diseases, but they all have significant physical and psychological ramifications, such as permanent scarring, poor self-image, social inhibition, depression, anxiety, and suicidal tendencies. Therefore, they are regarded as serious medical disorders.

Topical therapy is inevitable in acne treatment, especially in cases of mild to moderate acne. In more severe forms, a combined topical and systemic therapy is recommended. The success of therapeutics in the treatment of acne and related skin disorders, is highly dependent on a regular application of the topical agents over a prolonged period of time. The available treatments for acne and related skin disorders are mostly based on antibiotics and retinoids. However, some pharmaceutical products, such as spironolactone, are still used orally for treatment of cutaneous disorders such as acne, hirsutism and androgenic alopecia.

Hence, there is a need to provide a topical formulation including an effective agent that is simple to use, has a high skin permeation and drug release, and can therefore be used to effectively remove skin disorders and lesions.

SUMMARY

In one general aspect of the present application, a drug formulation in a form of a gel or lotion is disclosed. The formulation includes a nano-structured lipid carrier (NLC) matrix and spironolactone active ingredient loaded within the NLC matrix, forming spironolactone-loaded NLC (SP-NLC) particles. The SP-NLC nanoparticles are dispersed within a medium, forming a SP-NLC gel or lotion. In certain examples, SP-NLC particles may have a particle size in a range of about 50 to 950 nanometers.

The above general aspect may include one or more of the following features. In certain cases, the NLC matrix may include a solid lipid, a liquid lipid, and at least two emulsifier agents. In addition, the medium may include an essence, a preservative agent, a gelling agent; and deionized water.

The spironolactone active ingredient may be present in a range of about 0.1 to 5 percent by weight of the SP-NLC gel or lotion.

The solid lipid may be present in a range of about 0.28 to 20 by weight percent based on the weight of the SP-NLC gel or lotion and may be selected from the group consisting of of an aliphatic alcohol having about 14 to 30 carbon atoms; a wax; a solid or hard paraffin; a synthetic ester; a fatty acid having about 12 to 30 carbon atoms; a monoglyceride, diglyceride, or a triglyceride of a saturated fatty acid having about 10 to 30 carbon atoms; and mixtures thereof. In certain examples, the solid lipid may be selected from the group consisting of cetostearyl alcohol, carnauba wax, cetyl palmitate, stearic acid, glyceryl trilaurate, Tricaprin, Trilaurin, Trimyristin, Tripalmitin, Tristearin, a hydrogenated cocoglyceride, Witepsol® W 35, Witepsol® H 35, Witepsol® H 42, Witepsol® E 85, Glyceryl monostearate, Glyceryl behenate, Glyceryl palmitostearate, Palmitic acid, Decanoic acid, Behenic acid, Acidan N12, and mixtures thereof.

The liquid lipid may be present in a range of about 0.12 to 10 weight percent based on the weight of the SP-NLC gel or lotion and in certain cases may be selected from the group consisting of hydrogenated castor oil, oleic acid, Miglyol 812, and Casserole oil.

In certain examples, the emulsifier agents may have a hydrophilic-lipophilic balance (HLB) number in a range of about 2 to 18. In some cases, the HLB number may be in a range of about 4.3 to 18. In addition, at least one of the emulsifier agents may be a lipophilic emulsifier, and in some cases, at least one is a hydrophilic emulsifier. The emulsifier agents may include a non-ionic emulsifier. In some cases, the emulsifier agents may include polyoxyethylene sorbitan fatty acid esters, polyoxyethylene alkyl ethers, polyoxyethylene fatty acid esters, sorbitan esters, sucrose esters, lecithins, silicone surfactants, betains, polyglycerol fatty acid esters, or mixtures thereof. In some examples, the emulsifier agents may include TWEEN 80, BRIJ 97, CETOMACROGOL 1000, MYRJ 52, SPAN 80, WASANG ESTER7, Soybean lecithin, Egg lecithin, Phosphatidylcholine, Poloxamer 188, Poloxamer 182, Poloxamer 407, Poloxamine 908, Tyloxapol, Polysorbate 20, Polysorbate 60, Polysorbate 80, Sodium cholate, Sodium glycocholate, Taurocholic acid sodium salt, Butanol, Butyric acid, Dioctyl sodium sulfosuccinate, Monooctylphosphoric acid sodium, or mixtures thereof.

The lipophilic emulsifier may be present in a range of about 0.25 to 10 by weight percent based on the weight of the SP-NLC gel or lotion and the hydrophilic emulsifier may be present in an amount in a range of about 0.5 to 20 weight percent of the SP-NLC gel or lotion.

In certain cases, the gelling agent may be selected from the group consisting of acacia, alginic acid, bentonite, a carbomer, carboxymethyl cellulose, ethylcellulose, gelatin, hydroxyethyl cellulose, hydroxypropyl cellulose, magnesium aluminum silicate, methylcellulose, a poloxamer, polyvinyl alcohol, sodium alginate, tragacanth, and xanthan gum. The gelling agent may be is a polyacrylic acid, and may be present in a range of about 0.1 to 1.0 weight percent of the SP-NLC gel or lotion.

The preservative agent may be methyl paraben, ethyl paraben, propyl paraben, butyl p-hydroxy-benzoate, or mixtures thereof, and, in some examples, may be present in a range of about 0.1 to 0.2 percent weight of the SP-NLC gel or lotion.

The essence may be rosemary or lavender and, in certain cases, may be present in a range of about 0.01 to 0.05 weight percent of the SP-NLC gel or lotion.

The deionized water may be present in a range of about 61 to 97 weight percent of the SP-NLC gel or lotion.

In another general aspect of the present application, a method for preparation of a SP-NLC drug formulation is disclosed. The method includes steps of: melting a solid lipid into a mixture including a liquid lipid and spironolactone in the presence of a lipophilic emulsifier to form a molten lipidic phase; vigorously dispersing the molten lipidic phase in an aqueous phase to form a pre-emulsion; adding an essence to the pre-emulsion and vigorously dispersing the essence in the pre-emultion to form a stable first emulsion; cooling the first emulsion until the lipid droplets solidify, thereby forming a second emulsion including lipid nanoparticles incorporating spironolactone; dispersing a mixture of a gelling agent and a preservative agent into the second emulsion to form a third emulsion; and neutralizing the third emulsion to yield SP-NLC based gel or lotion.

In another general aspect of the present application, a method of treating a dermal disease with a therapeutically effective amount of a spironolactone-loaded NLC (SP-NLC) gel or lotion is disclosed. The method includes topically administrating the SP-NLC gel or lotion onto lesions. The lesions may have been caused by acne, rosacea, hirsutism, androgenic alopecia, or other dermal diseases. The effective amount of spirolactone active ingredient may vary in a range of about 1.0 to 3.0 by weight percent of the gel or lotion.

BRIEF DESCRIPTION OF THE DRAWINGS

FIG. 1 illustrates a schematic of an example SP-NLC gel or lotion formulation, including SP-NLC particles dispersed within a medium. The SP-NLC particles include nano-structured lipid carrier (NLC) matrix incorporating the spironolactone active ingredient, thereby forming a spironolactone-loaded NLC (SP-NLC) particle. In the example illustrated in FIG. 1, the SP-NLC includes a solid lipid (designated by the symbol □), a liquid lipid (designated by the symbol), emulsifiers (designated by the symbol ○), and the spironolactone active ingredient (designated by the symbol).

DETAILED DESCRIPTION

The following detailed description is presented to enable a person skilled in the art to make and use the application. For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. The present application is not intended to be limited to the implementations shown, but is to be accorded the widest possible scope consistent with the principles and features disclosed herein.

Most of the anti-acne agents are virtually insoluble in water, and thus difficult to be incorporated into aqueous systems. Spironolactone, which is an anti-androgen drug, has commonly been used orally for more than 20 years, in the form of tablets for the treatment of cutaneous disorders such as acne, hirsutism and androgenic alopecia. However, due to its low solubility in water (which is about 2.8 mg/100 ml), it is poorly absorbed from the gastrointestinal tract. Furthermore, it has some endocrine side effects, including menstrual irregularity, breast tenderness, gynecomastia, headache and fatigue, all of which restrict its clinical application.

One promising route of spironolactone administration may be topical delivery, which allows high drug levels at the site of action, and it decreases the systemic side effects and also improves the patient's compliance. Solid lipid nanoparticles (SLNs) and Nanostructured lipid carriers (NLCs) have been investigated as carriers for hydrophilic and lipophilic drugs in a topical form, and the aforementioned carriers are well suited for use on inflamed and damaged skin, because of their small size, and safe materials. The small particle size of these carriers, ensures close contact with the stratum corneum, and due to the formation of an intact film on the skin surface upon drying, the amount of encapsulated compounds penetrating into the skin increases.

To this end, the present application provides spironolactone active ingredient loaded onto a nano-structured lipid carrier (SP-NLC) in a form of a topical gel or lotion, which is effective against acne and other skin disorders such as rosacea, androgenic alopecia, and hirsutism that respond to anti-androgens.

In one implementation, the present application provides spironolactone active ingredient loaded onto a nano-structured lipid carrier (SP-NLC) in a form of a gel or lotion, which enables the contact of an effective amount of spironolactone on the desired site on patient's skin.

In another implementation, the present application provides a spironolactone active ingredient loaded onto a nano-structured lipid carrier (SP-NLC) in a form of a gel or lotion that is adsorbed by skin where it is applied, without any undesirable skin irritation and systemic side effects.

Figure 1:
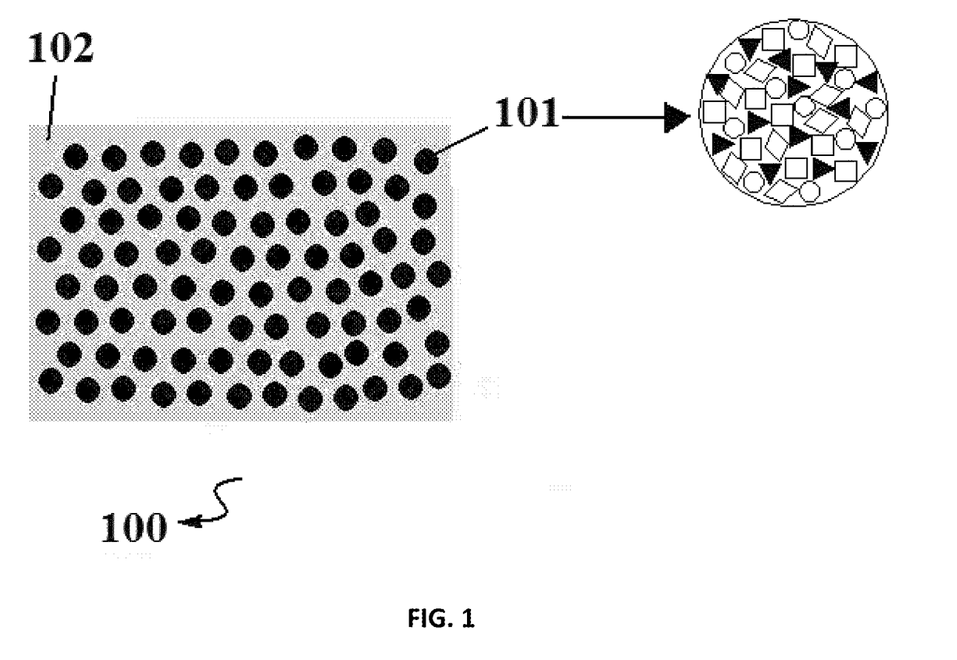

FIG. 1 illustrates a schematic of one example of a spironolactone loaded nano-structured lipid carrier (SP-NLC) gel or lotion formulation 100. The nano-structured lipid carrier (NLC) matrix incorporating the spironolactone active ingredient, thereby forming a spironolactone-loaded NLC (SP-NLC) particle 101. In the example illustrated in FIG. 1, the SP-NLC particle 101 includes: a solid lipid (designated by the symbol □), a liquid lipid (designated by the symbol), at least two emulsifiers (designated by the symbol ○), and the spironolactone active ingredient (designated by the symbol) loaded onto the NLC matrix. In certain cases, the SP-NLC particles may have a particle size in a range of about 50 to 950 nanometers.

Referring again to FIG. 1, in certain examples, the gel or lotion medium 102 may contain deionized water, essence, a preservative agent and a gelling agent.

The solid lipid of the SP-NLC formulation represented in FIG. 1 may be one of various compounds. In certain examples, the solid lipid may be a high saturated alcohol. In particular, in certain cases it may be an aliphatic alcohol having about 14 to 30 carbon atoms, such as cetostearyl alcohol. In other cases, the solid or hard lipid may be a wax, such as carnauba wax. In some examples, the solid lipid may be a hydrocarbon such as a solid or hard paraffin. In some cases the solid paraffin may include paraffin wax. In other cases, the solid paraffin may include a soft paraffin such as petroleum jelly. In other examples, the solid or hard lipid may be a synthetic ester, such as cetyl palmitate. In certain examples of the SP-NLC, the hard or solid lipid may include a higher fatty acid. The higher fatty acid may be a mono-carboxylic acid containing an unbroken or acyclic chain of at least 7 carbon atoms bonded to a carboxyl group such as lauric, palmitic, stearic, oleic, ricinoleic, linoleic, and behenolic acids. In certain cases, the higher fatty acid may have about 12 to 30 carbon atoms. In some cases, the higher fatty acid may be stearic acid. In certain examples of the SP-NLC, the hard or solid lipid may be a mono-, di- or triglyceride of a higher saturated fatty acid having about 10 to 30 carbon atoms, such as glyceryl trilaurate. In certain examples, the solid or hard lipid may include Tricaprin, Trilaurin, Trimyristin, Tripalmitin, Tristearin, a hydrogenated coco-glyceride such as Softisan® 142, a suppository base such as Witepsol® W 35, Witepsol® H 35, Witepsol® H 42, Witepsol® E 85, Glyceryl monostearate (such as Imwitor®900), Glyceryl behenate (such as Compritol® 888 ATO), Glyceryl palmitostearate (such as Precirol® ATO 5), Palmitic acid, Decanoic acid, Behenic acid, Acidan N12, or mixtures thereof.

The liquid lipid of the SP-NLC formulation represented in FIG. 1 may include hydrogenated castor oil, oleic acid, Miglyol 812, or Casserole oil, but is not limited thereto.

In one implementation, at least one of the emulsifier agents is a hydrophilic emulsifier and another one is a lipophilic emulsifier. In certain cases, the emulsifier agents may have a HLB (Hydrophilic-Lipophilic Balance) number in a range of about 2 to 18, and in some cases, a HLB number ranging of about 4.3 to 18.

The emulsifier agents may include non-ionic emulsifiers. In certain cases, the emulsifier agents may include polyoxyethylene sorbitan fatty acid esters such as TWEEN 80; polyoxyethylene alkyl ethers such as BRIJ 97 or CETOMACROGOL 1000; polyoxyethylene fatty acid esters such as MYRJ 52; sorbitan esters such as SPAN 80; or sucrose esters such as WASANG ESTER7. The emulsifiers may alternatively or additionally include lecithins including Soybean lecithin such as Lipoid® S 75 or Lipoid® S 100. The emulsifiers may include Egg lecithin such as Lipoid® E 80. In some cases the emulsifiers may include Phosphatidylcholine such as Epikuron® 170 or Epikuron 200. The emulsifiers may additionally or alternatively include Poloxamer 188, Poloxamer 182, Poloxamer 407, Poloxamine 908, Tyloxapol, Polysorbate 20, Polysorbate 60, Polysorbate 80, Sodium cholate, Sodium glycocholate, Taurocholic acid sodium salt, Butanol, Butyric acid, Dioctyl sodium sulfosuccinate, Monooctyl phosphoric acid sodium, silicone surfactants, betains, polyglycerol fatty acid esters, or mixtures thereof.

Referring again to FIG. 1, in certain examples, the gel or lotion 102 may include deionized water, essence, a preservative agent and a gelling agent. The preservative agent may be one or more of the compounds of methyl paraben, ethyl paraben, propyl paraben and butyl p-hydroxy-benzoate.

The gelling agent may be acacia, or alginic acid, or bentonite, or carbomers such as Carbopol® polyacrylic acids, or carboxymethyl cellulose, or ethylcellulose, or gelatin, or hydroxyethyl cellulose, or hydroxypropyl cellulose, or magnesium aluminum silicate such as Veegum®, or methylcellulose, or poloxamers such as Pluronics®, or polyvinyl alcohol, or sodium alginate, or tragacanth, or xanthan gum. In certain cases, the gelling agent may be Carbopol® polyacrylic acids and may be present in an amount of about 0.1 to 1.0 weight percent, based on the total weight of the gel or lotion.

In one implementation, the essence may be rosemary or lavender in an amount of about 0.01 to 0.05 weight percent, based on the total weight of the gel or lotion.

Figure 2:
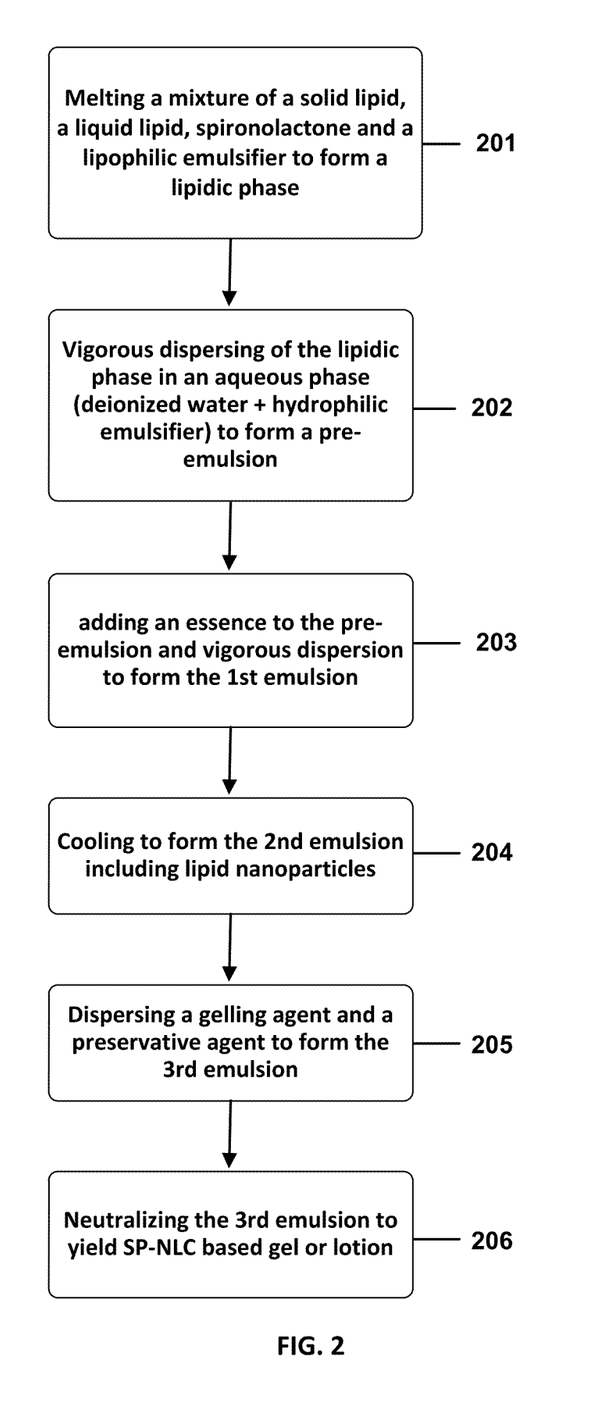
FIG. 2 illustrates an example preparation method for a SP-NLC gel or lotion prepared pursuant to the teachings of the present application.

FIG. 2 shows an example process for preparation of the topical SP-NLC formulation disclosed in the present application as described above. In the first step 201, a mixture including a solid lipid, a liquid lipid, spironolactone, and a lipophilic emulsifier is melted to form a molten lipidic phase. The solid lipid may be present in an amount of about 0.28 to 20 by weight percent based on the total weight of the gel or lotion. The liquid lipid may be present in an amount of about 0.12 to 10 weight percent of the total gel or lotion weight. The spironolactone may be present in an amount of about 0.1 to 5 percent by weight of the total gel or lotion. The lipophilic emulsifier may be present in an amount of about 0.25 to 10 by weight percent of the gel or lotion. In certain examples, the ratio of the solid lipid to the liquid lipid may be in a range of about 50:50 to 99:1 by weight percent.

The second step 202 involves vigorous dispersing of the molten lipidic phase obtained from step 201 in an aqueous phase to form a pre-emulsion. The aqueous phase may include deionized water and a hydrophilic emulsifier, where the weight percent of water may be about 61 to 97 percent based on the total weight of the gel or lotion and the hydrophilic emulsifier may be present in an amount of about 0.5 to 20 by weight of the gel or lotion. In certain cases, the vigorous dispersion may be done via mechanical mixing using a homogenizer device following by a higher pressure homogenizer valve machine or a probe-ultrasonicator.

The third step 203 involves adding an essence to the pre-emulsion obtained from step 202 following by vigorous dispersion to form a stable first emulsion. In certain cases, the vigorous dispersion may be done via a method as described in step 202 hereinabove. In certain examples, the essence may be rosemary or lavender with an amount of about 0.01 to 0.05 weight percent, based on the total weight of the gel or lotion.

The fourth step 204 involves cooling the first emulsion resulting from step 203 until the lipid droplets solidify, thereby forming a second emulsion including lipid nanoparticles incorporating spironolactone. In certain cases, the cooling may be done via natural convection in an ambient temperature of about 25 C.

The fifth step 205 involves dispersing a gelling agent in a mixture with a preservative agent to the second emulsion resulting from step 204 to form a third emulsion. The gelling agent may be present in an amount of about 0.1 to 1.0 weight percent based on the total weight of the gel or lotion. In addition, the preservative agent may be present in an amount in a range of about 0.1 to 0.2 percent by weight of the gel or lotion.

The sixth step 206 involves neutralizing the third emulsion obtained from step 205 to yield a SP-NLC based gel or lotion. In some cases, the neutralizing may be performed by addition of a neutralizing agent such as tri-ethanolamine.

In another implementation of the present application, examples of the SP-NLC formulation introduced and prepared pursuant to the present application can be used for treatment of skin disorders and dermal diseases, such as acne, rosacea, hirsutism, androgenic alopecia, etc. The treatment can be done via topical administration of a therapeutically effective amount of the spironolactone-loaded NLC (SP-NLC) formulation in form of, for example, a gel or a lotion.

The effective amount of the SP-NLC gel or lotion formulation depends on the type of the dermal disease. For example an effective amount of spironolactone loaded may be about 1.0 by weight percent based on the weight of the gel or lotion for acne treatment. However, other amounts of spironolactone loaded into the SP-NLC formulation may also be effective in treating acne. Generally, an effective amount for spironolactone active ingredient in a range of about 1.0 to 3.0 by weight percent based on the weight of the gel or lotion may be used for dermal disease treatments.

Some examples of applications of the SP-NLC formulations disclosed herein are illustrated below. The examples provided in this specification are not to be considered limiting the scope of the application but are to be considered as illustrative of how the application is to be carried out with the specifically described examples. Any equivalents that can be used to get the same function or variations obvious to a person skilled in the art are to be considered included within the scope of this specification and claims.

Example 1: Preparation of SP-NLC Nanogel or Nanolotion as a Topical Formulation

Table 1 illustrates representative preparations of a nano-structured lipid carrier (NLC) incorporating spironolactone active agent in a form of a nanogel (formulation "A") or nanolotion (formulation "B") in accordance with the present application. In addition, a solid lipid nanoparticles (SLNs) incorporating spironolactone active agent (SP-SLN) in a form of a conventional gel (formulation "C") and an alcoholic formulation containing 5% of SP (SP-ALC) (formulation "D") were prepared for further comparison of their properties and therapeutic effects.

In one example, the nano-structured lipid carrier (NLC) incorporating spironolactone (SP-NLC) in a form of nanogel or nanolotion may be prepared as: A mixture of stearic acid (a solid lipid) and oleic acid (a liquid lipid) with spironolactone in the presence of Span 80 (a lipophilic emulsifier) was melted at 85 C to obtain a lipidic phase. An aqueous phase was prepared separately by dissolving of Tween 80 (a hydrophilic emulsifier) in deionized water. Thereafter, the molten lipidic phase was dispersed vigorously in the aqueous phase using a probe-ultrasonicator to form a pre-emulsion. Then, Lavender (an essence) was added to the pre-emulsion and again sonicated by probe-ultrasonicator to obtain a stable emulsion. The stable emulsion was cooled in the ambient temperature to solidify the lipid droplets and resulting an emulsion including lipid nanoparticles incorporating spironolactone. Then, Carbopol (a gelling agent) within a mixture with Methyl paraben (a preservative agent) was dispersed in the obtained emulsion. The emulsion was then neutralizied using Triethanolamine to yield a spironolactone-loaded NLC based gel or lotion.

Figure 3A:
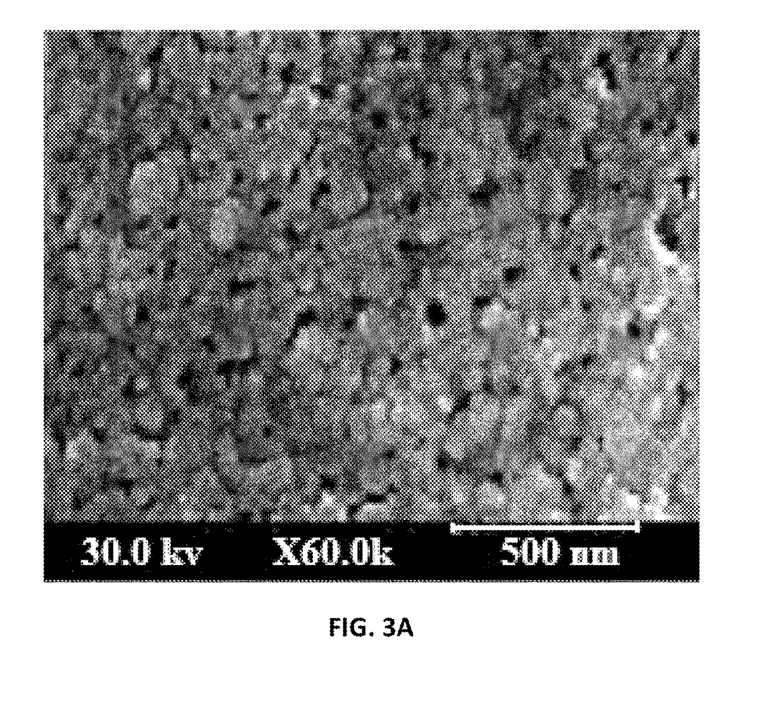
FIG. 3A illustrates a field emission scanning electron microscopy (FESEM) micrograph of an example of raw spironolactone (SP) material (the particles visualized at 30 kv and magnification 500 nm).
Figure 3B:
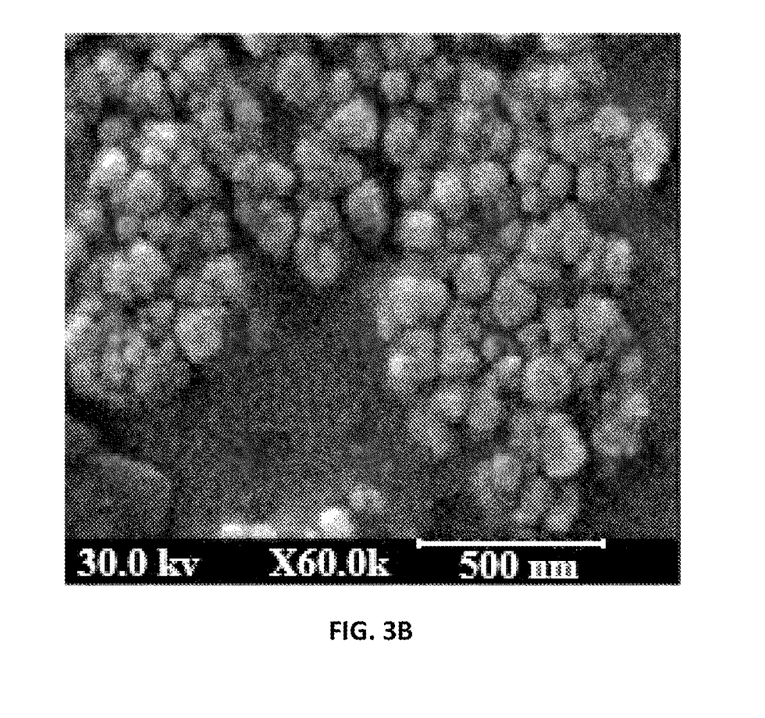
FIG. 3B illustrates a field emission scanning electron microscopy (FESEM) micrograph of an example solid lipid nanoparticles matrix (SLNs) incorporating spironolactone active ingredient (SP-SLN) (the particles visualized at 30 kv and magnification 500 nm).
Figure 3C:
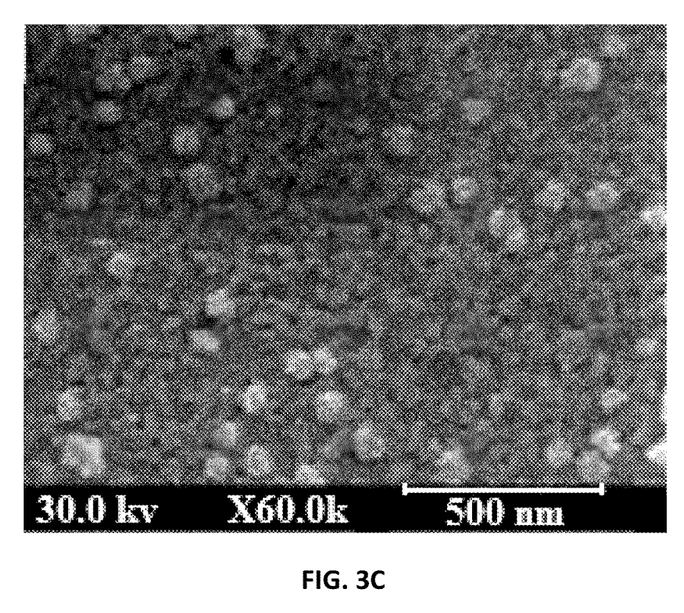
FIG. 3C illustrates a field emission scanning electron microscopy (FESEM) micrograph of an example NLC matrix incorporating spironolactone active ingredient (SP-NLC) prepared pursuant to teachings of the present application (the particles visualized at 30 kv and magnification 500 nm).

FIGS. 3A, 3B and 3C illustrate comparative FESEM micrographs of raw spironolactone (SP) (FIG. 3A), a SP-SLN (FIG. 3B) and a SP-NLC (FIG. 3C). These figures show that by increasing the proportion of liquid lipid in SP-NLC structure compared with SP-SLN, SP particles exhibit spherical shape and low and narrow size distribution within the lipidic matrix.

TABLE 1

| | Formulation (wt/wt %) | | | |
|---|---|---|---|---|
| Ingredients | A (SP-NLC-gel) | B (SP-NLC-lotion) | C (SP-SLN) | D (SP-ALC) |
| Spironolactone | 1 | 1 | 1 | 5 |
| Stearic acid | 2 | 2 | 4 | — |
| Oleic acid | 2 | 2 | — | — |
| Lavender essence | 0.02 | 0.02 | 0.02 | — |
| Tween 80 | 5 | 5 | 5 | — |
| Span 80 | 2.5 | 2.5 | 2.5 | — |
| Carbopol | 1 | 0.1 | 1 | 1 |
| Methyl paraben | 0.2 | 0.2 | 0.2 | 0.2 |
| Triethanolamine | 0.2 | 0.2 | 0.2 | — |
| hydroxyethyle cellulose | — | — | — | 5 |
| propylen glycol | — | — | — | 10 |
| Deionized Water | 86.08 | 86.98 | 86.08 | 78.80 |

Example 2: Drug Release Behavior

In this example, the in vitro releases of SP from SP-NLC, SP-SLN and SP-ALC gels, prepared according to the previous example, were studied by employing dialysis tube diffusion techniques. About 10 mg of each gel was individually kept in a dialysis membrane (MW cut-off 12 000) which was tied at both ends and placed in a separate beaker containing about 100 ml simulated intestinal fluid (pH=about 6.8). The beakers were assembled above a magnetic stirrer in order to continuous stirring at 60 rpm and maintaining constant temperature of about 32±3° C. The samples were withdrawn at predetermined time intervals (0.5, 1, 2, 4, 6, 8 and 24 h), filtered (pore size: 0.22 μm) and the concentration of SP was determined using the HPLC method.

Figure 4:
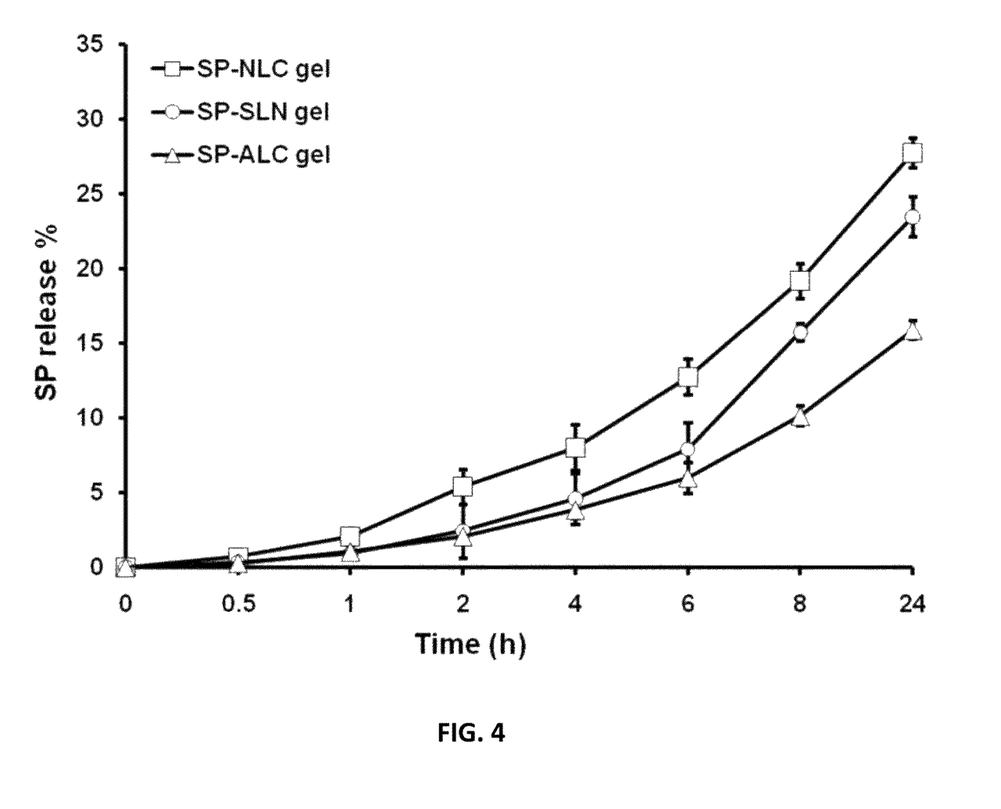
FIG. 4 illustrates an in vitro release profile of SP from SLN (SP-SLN), NLC (SP-NLC) and alcoholic (SP-ALC) gels, prepared pursuant to teachings of the present application, across a dialysis membrane (MWCO 12-14000). Values are expressed as mean±standard deviation (n=3).

The SP release percentage from SP-NLC, SP-SLN and SP-ALC gels is illustrated in FIG. 4. This figure show a much higher release of SP from SP-NLC compared to both SP-SLN and SP-ALC gels.

Example 3: In Vitro Skin Permeation and Deposition Study

In vitro skin permeation of SP from SLN, NLC and alcoholic based gels were evaluated using hairless abdominal rat skin. For this purpose, skin from the abdominal area of Wistar male rats, weighing about 200-250 g, was used. After anesthetizing the rats with ether, the abdominal skin shaved using electric and hand razors. In the next stage, the skin was surgically removed and to remove the adhering subcutaneous debris and leachable enzymes dermal side of the skin was put in contact with a saline solution at about 4° C. for about 24 hours before starting the diffusion experiment. The skin specimens were thus prepared and individually placed in Franz diffusion cells having a surface area 3.14 cm². The excised rat skin was set in place with the stratum corneum facing the donor compartment and the dermis facing the receptor. The receiver compartment was filled with about 5.5 ml of PBS (pH 7.4). The diffusion cells were maintained at about 37±0.5° C. with stirring at about 300 rpm throughout the experiment. The specialized amount of various formulations was applied onto the rat skin in the donor compartment. Samples from receiver medium were withdrawn (about 3 ml) at predetermined time intervals (0, 1, 2, 3, 4, 6, 8 and 24 hours) and an equivalent volume of fresh PBS maintained at about 37° C. was replaced. All samples were filtered through an aqueous 0.22 μm filter and analyzed by HPLC method. To calculate the amount of drug deposited within the skin, the skins were removed and washed three times with phosphate buffer solution (PBS, pH 7.4) and residual washing solvent was carefully wiped off from the skin with a cotton swab. The skins were minced, transferred to a test tube and digested 24 hours in 1 ml of PBS (pH 7.4) and 1 ml of HCl 0.1M. All the samples were then centrifuged at 25000 rpm for about 20 min. The supernatant filtered through 0.22 μm membrane and quantified by HPLC at 238 nm for SP content.

Figure 5:
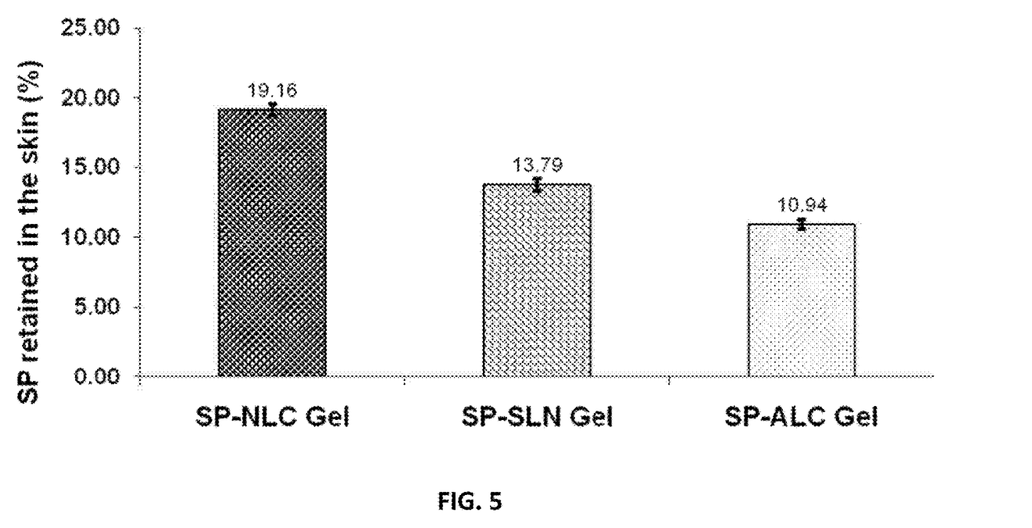
FIG. 5 illustrates the percentage of SP retained in the skin for the SP-NLC, SP-SLN and SP-ALC gels after in vitro skin-permeation study. Values are expressed as mean±standard deviation (n=3).

FIG. 5 shows the percentage of SP retained in the skin for the gels after in vitro skin-permeation study. The values are expressed as mean±standard deviation (n=3). The values of this figure show a higher retained value (19.16%) by the skin at the end of the in vitro skin-retention study (after about 24 hours) for the SP-NLC gel compared with 13.79% for SP-SLN and 10.94% for SP-ALC gels.

Example 4: Investigation of the Therapeutic Effect of SP-NLCs

In this example, Seventy six patients between 11 and 38 years old, with mild and moderate acne defined as a score of 1-30 on the global acne grading system (GAGS) scale recruited in the present application by a single investigator of which 70 women and 6 men were treated using a SP-NLC gel including 1% spironolactone and a conventional gel SP-ALC including 5% spironolactone, prepared in accordance with example 1 hereinabove. Before groups design, patients who had received systemic or topical anti acne therapy 3 months before or during the study, who were pregnant or planning to become pregnant and lactating, who had a skin disease that might interfere with the diagnosis or evaluation of their hyperpigmentation were excluded from the study. Patients who were not satisfied with their previous acne therapies participated in the double-blind clinical trial study after giving written informed consent. At the first visit, a detailed questionnaire including data of demographic status, acne duration and medical history was completed for each patient. Both the physicians and patients were blinded to the type of treatment. Every morning and evening, patients washed their face with non-medicated soap, then thoroughly rinsed and dried it. Over the 8-week course, a patient applied 2 tubes of gel and was asked to apply about 2 cm of the gel each morning and evening to the beard area and massage it for about 2 minutes. They were left on individual acne lesions for 2-3 hours, after which they were washed off. Non-medicated cosmetics were permitted during the study. The patients were asked about adherence to the protocol and to report any side effects. During the trial the patients were prohibited from using any drugs or other skin care treatments for acne. The patients were assessed for any changes in the facial lesion counts (non-inflammatory lesions: open and closed comedones; inflammatory lesions: papules, pustules, and nodules) at each clinic visit (0, 2, 4 and 8 wk). At every session, the acne lesions were assessed based on their numbers.

The patients were assessed for any changes in the facial lesion counts (non-inflammatory lesions, including: open and closed comedones; and inflammatory lesions, including: papules, pustules, and nodules) at each clinic visit (0, 2, 4 and 8 wk). At every session, the acne lesions were assessed based on their numbers, type and distribution.

Figure 6:
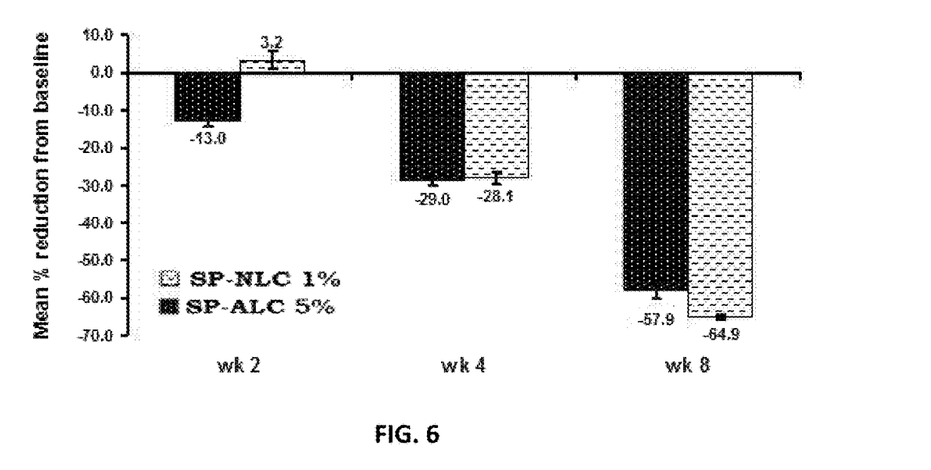
FIG. 6 illustrates Mean percentage changes in total lesion scores from baseline using SP-NLC 1% and SP-ALC 5% prepared pursuant to teachings of the present application at different sessions (2, 4 and 8 weeks).

The mean percentage changes in total lesion scores from baseline using SP-NLC 1% and SP-ALC 5% are summarized in FIG. 6. At baseline, the mean scores of total (inflammatory and non-inflammatory) lesions was 37.66±9.27 for group treated by SP-NLC 1%, and 33.73±9.40 for group treated by SP-ALC 5%. It can be seen from this figure that in both groups, the percentage reduction of total lesion scores after week 8th compared to the baseline was significant and much greater that previous time intervals (2 and 4 weeks).

For the final assessment and to determine the efficacy of the treatment, the following formula was used for Total Lesion Count:

Total Lesion Count (TLC)=comedones+papules+pustules

Figure 7:
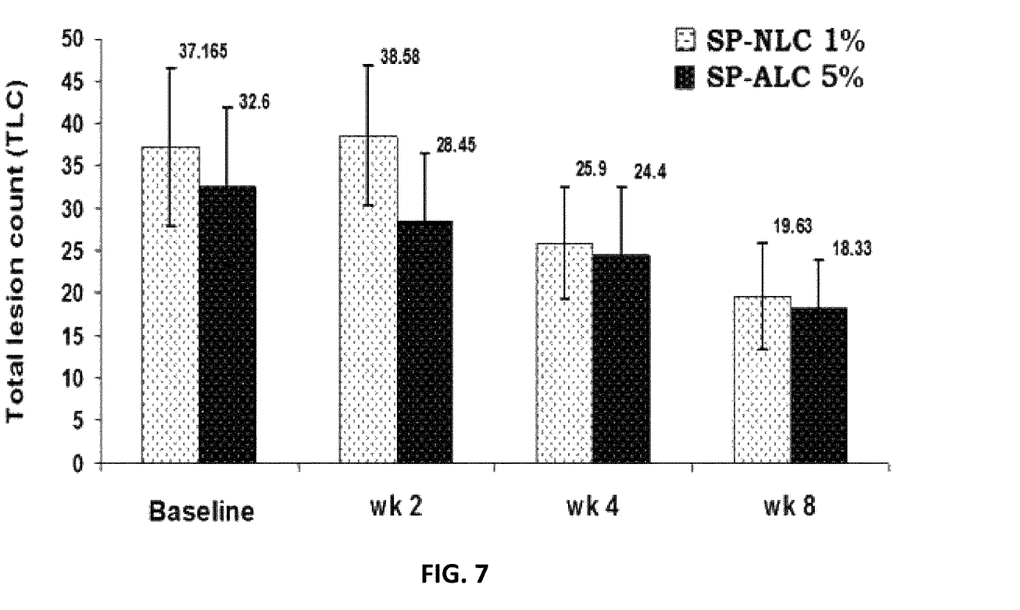
FIG. 7 illustrates total lesions count (TLC) for acne treatment using SP-NLC 1% and SP-ALC 5% prepared pursuant to teachings of the present application at different sessions (0, 2, 4 and 8 weeks).

FIG. 7 illustrates the acne lesions counts initially and after every 2 weeks. Referring again to this figure, the clinical response is highly positive in total lesion count in both groups treated by the SP-NLC and SP-ALC gels containing 1% and 5% of spironolactone, but about 58% and 65% of their total lesion scores showed clinical improvement after 8 weeks. This figure shows a statistically significant difference between the two sessions (week 8 compare to baseline) in the both groups towards a decrease of the total lesion count. The means of the TLC in the group treated by SP-NLC are 37.165±9.28 for the first session to 19.63±6.36 for the last session, which showed a statistically significant difference towards a decrease of the lesions using the SP-NLC gel including only 1% spironolactone. Furthermore, this figure also shows a statistically significant decrease in TLC for the group treated by SP-ALC gel from 32.60±9.32 to 18.33±5.56, where 5% spironolactone was incorporated in the gel formulation.

In addition, it should be considered that there were no serious adverse experiences that were related to B treatment. In contrast, dryness and itching were the most frequent symptoms reported in A groups. Serum and urine samples were taken from 10 patients in each group before treatment and 2 month after treatments respectively. No trace of spironolactone and its metabolite, carenon were detected at any time by a high pressure liquid chromatography technique.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A topical formulation for treating one or more dermal diseases, comprising:
 a nano-structured lipid carrier (NLC) matrix, the NLC matrix including:
  a solid lipid,
  a liquid lipid, comprising oleic acid and
  at least two emulsifier agents, including a lipophilic emulsifier and a hydrophilic emulsifier;
 spironolactone as an active ingredient incorporated within the NLC matrix, forming spironolactone-loaded NLC (SP-NLC) particles with a particle size in a range of less than 300 nanometers; and
 a medium, including:
  an essence, including rosemary or lavender,
  a preservative agent,
  a gelling agent, and
  deionized water,
 wherein:
  the dermal disease comprises Acne, comprising mild to moderate Acne vulgaris,
  the SP-NLC particles are dispersed within the medium, forming a SP-NLC gel or lotion,
  the solid lipid is present with an amount of less than 4 percent based on the weight of the SP-NLC gel or lotion,
  the liquid lipid is present with an amount of 2 percent or less based on the weight of the SP-NLC gel or lotion,
  the spironolactone is present with a therapeutically effective amount of 1.0 percent by weight of the SP-NLC gel or lotion,
  the preservative agent is present in a range of about 0.1 to 0.2 percent by weight of the SP-NLC gel or lotion,
  the gelling agent is present in a range of about 0.1 to 1.0 percent by weight of the SP-NLC gel or lotion, and
  the deionized water is present with an amount of 80 percent or more based on the weight of the SP-NLC gel or lotion.

2. The formulation according to claim 1, wherein the SP-NLC particles have a particle size in a range of about 50 to 299 nanometers.

3. The formulation according to claim 1, wherein the solid lipid is selected from the group consisting of a fatty acid having about 12 to 30 carbon atoms; a monoglyceride, diglyceride, or a triglyceride of a saturated fatty acid having about 10 to 30 carbon atoms, and mixtures thereof.

4. The formulation according to claim 3, wherein the solid lipid is selected from the group consisting of cetyl palmitate, stearic acid, glyceryl trilaurate, Tricaprin, Trilaurin, Trimyristin, Tripalmitin, Tristearin, a hydrogenated cocoglyceride, Glyceryl monostearate, Glyceryl behenate, Glyceryl palmitostearate, Palmitic acid, Decanoic acid, Behenic acid, monostearate monocitrate diglyceride, and mixtures thereof.

5. The formulation according to claim 1, wherein the solid lipid is present in a range of about 0.28 to 4 weight percent based on the weight of the SP-NLC gel or lotion.

6. The formulation according to claim 1, wherein the liquid lipid includes a fatty acid having about 12 to 30 carbon atoms.

7. The formulation according to claim 1, wherein the liquid lipid is present in a range of about 0.12 to 2 weight percent based on the weight of the SP-NLC gel or lotion.

8. The formulation according to claim 1, wherein the emulsifier agents have a hydrophilic-lipophilic balance (HLB) number in a range of about 2 to 18.

9. The formulation according to claim 8, wherein the HLB number is in a range of about 4.3 to 18.

10. The formulation according to claim 1, wherein the lipophilic emulsifier is selected from the group consisting of polyoxyethylene sorbitan fatty acid esters, sorbitan esters, sucrose esters, lecithins, silicone surfactants, betains, polyglycerol fatty acid esters, polyoxyethylene (20) sorbitan monooleate, soybean lecithin, egg lecithin, and mixtures thereof.

11. The formulation according to claim 1, wherein the hydrophilic emulsifier is selected from the group consisting of polyoxyethylene sorbitan fatty acid esters, a Poloxamer Tyloxapol, a Polysorbate, and mixtures thereof.

12. The formulation according to claim 1, wherein the preservative agent is selected from the group consisting of methyl paraben, ethyl paraben, propyl paraben, and mixtures thereof.

13. The formulation according to claim 1, wherein the gelling agent is selected from the group consisting of carboxymethyl cellulose, ethylcellulose, hydroxyethyl cellulose, hydroxypropyl cellulose, carbomers, and methylcellulose.

14. The formulation according to claim 1, wherein the gelling agent includes carbomers, and is present in amount of about 1.0 weight percent based on the total weight of the SP-NLC gel, or about 0.1 weight percent based on the total weight of the SP-NLC lotion.

15. The formulation according to claim 1, wherein the essence is present in a range of about 0.01 to 0.05 weight percent based on the total weight of the SP-NLC gel or lotion.

16. The formulation according to claim 1, wherein the deionized water is present in a range of about 80 to 97 weight percent based on the total weight of the SP-NLC gel or lotion.

17. A topical formulation for treating Acne, comprising a spironolactone-loaded NLC (SP-NLC) gel or lotion, the SP-NLC gel or lotion comprising:

SP-NLC particles with a particle size in a range of less than 300 nanometers, the SP-NLC particles comprising:
a nano-structured lipid carrier (NLC) matrix, the NLC matrix comprising:
a solid lipid, comprising stearic acid with an amount of 2 percent based on the weight of the SP-NLC gel or lotion;
a liquid lipid, comprising oleic acid with an amount of 2 percent based on the weight of the SP-NLC gel or lotion; and
at least two emulsifier agents, comprising a lipophilic emulsifier and a hydrophilic emulsifier; and
spironolactone incorporated within the NLC matrix with a therapeutically effective amount of 1.0 weight percent based on the weight of the SP-NLC gel or lotion; and
a medium, comprising:
an essence, comprising rosemary or lavender with an amount of 0.02 weight percent based on the total weight of the SP-NLC gel or lotion;
a preservative agent, comprising at least one of methyl paraben, ethyl paraben, propyl paraben, and mixtures thereof with an amount of 0.2 percent by weight of the SP-NLC gel or lotion;
a gelling agent comprising a carbomer with an amount in a range of 0.1 to 1.0 percent by weight of the SP-NLC gel or lotion; and
deionized water with an amount of 80 percent or more based on the weight of the SP-NLC gel or lotion,
wherein the SP-NLC particles are dispersed within the medium, forming the SP-NLC gel or lotion.

* * * * *